United States Patent [19]

Carr et al.

[11] Patent Number: 5,075,507
[45] Date of Patent: Dec. 24, 1991

[54] PROCESS FOR THE PREPARATION OF BIS(AMINOPROPYL)ALIPHATIC GLYCOLS

[75] Inventors: Richard V. C. Carr, Allentown; Thomas A. Johnson, Orefield; Steven M. Galaton, Doylestown; Thomas A. Albanese, Allentown, all of Pa.

[73] Assignee: Air Products and Chemicals, Inc., Allentown, Pa.

[21] Appl. No.: 226,641

[22] Filed: Aug. 1, 1988

[51] Int. Cl.$^5$ ............................................. C07C 209/48
[52] U.S. Cl. ..................................... 564/491; 564/490
[58] Field of Search ................................ 584/490, 491

[56] References Cited

U.S. PATENT DOCUMENTS

| | | | |
|---|---|---|---|
| 2,160,578 | 5/1939 | Schmidt | 564/493 X |
| 2,408,959 | 10/1946 | Stegemeyer | 564/493 |
| 3,163,676 | 12/1964 | Potts | 564/493 |
| 3,799,986 | 3/1974 | Poppelsdorf et al. | 260/584 B |
| 4,313,004 | 1/1982 | Kluger et al. | 564/491 |

FOREIGN PATENT DOCUMENTS 0212986  4/1987  European Pat. Off. ............ 564/493

OTHER PUBLICATIONS

Adams et al., "Organic Reactions", vol. IV, pp. 82-85, and 89-92 (1949).

Primary Examiner—Richard L. Raymond
Attorney, Agent, or Firm—Russell L. Brewer; James C. Simmons; William F. Marsh

[57] ABSTRACT

This invention relates to a process for the separation of acrylonitrile used in the cyanoethylation of glycols to produce a bis(cyanoethylated) aliphatic glycol from the resulting glycol which is then reduced with hydrogen to produce the corresponding bis(aminopropyl) aliphatic glycol. In this process, acrylonitrile is reacted with an aliphatic glycol in stoichiometric excess and the acrylonitrile removed from the cyanoethylated glycol by reaction with aliphatic primary or secondary amine prior to effecting the hydrogenation of the cyanoethylated aliphatic glycol in the presence of the acrylonitrile-amine reaction product. The reaction product then can be separated by conventional techniques such as distillation.

8 Claims, No Drawings

PROCESS FOR THE PREPARATION OF BIS(AMINOPROPYL)ALIPHATIC GLYCOLS

TECHNICAL FIELD

This invention relates to a process for producing a cyanoethylated glycol by the reaction of acrylonitrile and an aliphatic glycol which are subsequently hydrogenated to form the corresponding bis(aminopropyl)aliphatic glycol.

BACKGROUND OF THE INVENTION

U.S. Pat. No. 4,313,004 discloses a process for producing bis(aminopropyl)aliphatic glycols through a two step process comprising a first step of reacting acrylonitrile with an aliphatic glycol and then reducing the nitrile group by contacting the cyanoglycol with hydrogen in the presence of a hydrogenation catalyst. In this patent it is reported that various side reactions occur during the hydrogenation step and the extent of byproduct formation is increased where residual acrylonitrile is present. For example, cyanoalkylated glycols may undergo cleavage to form undesired glycols, amino alcohols, polyamines and impurities or the acrylonitrile may react with the amine generated in the reduction, thereby contaminating the reaction product and presenting a separation problem.

U.S. Pat. No. 3,799,986 discloses a process for preparing amines reacting an olefinic nitrile, such as acrylonitrile, with various polyhydroxy compounds followed by hydrogenation. In this process the olefinic nitrile is reacted with the polyhydroxy compound typically in stoichiometric proportions although excess of either can be utilized. After the condensation is completed, the olefinic nitrile is removed under reduced pressure. The patentees point out that it is sometimes difficult to remove the olefinic nitrile because of a tendency to polymerize and the polymerized nitrile impurity in the cyanoalkylated product may poison the hydrogenation catalyst during the hydrogenation step. In general the polymerized nitrile is removed by contacting the reaction mixture with solvents selective for the cyanoalkylated polyhydric alcohol reaction product such as saturated aliphatic and cycloaliphatic hydrocarbons. The hydrogenation then is carried out after removal of hydrocarbon solvent, typically in the presence of a tertiary amine or anhydrous ammonia. Ammonia and tertiary amine tend to minimize cleavage of the cyanoalkylated product during hydrogenation to the amine.

SUMMARY OF THE INSTANT INVENTION

This invention relates to an improvement in a process for preparing bis(aminopropyl) aliphatic alcohols wherein acrylonitrile is reacted with an aliphatic glycol and the resulting cyanoethylated glycol reduced to the corresponding amine by contacting the cyanoethylated glycol with hydrogen in the presence of a hydrogenation catalyst. The improvement resides in cyanoethylation stage wherein the acrylonitrile is present in substantial stoichiometric excess, at least 100% stoichiometric excess to form the corresponding cyanoethylated glycol. After the initial cyanoethylation reaction, the reaction product is contacted with a primary or secondary aliphatic amine for reaction with the remaining acrylonitrile and then said hydrogenation is accomplished by contacting the reaction mixture including, the reaction product of acrylonitrile and aliphatic primary and/or secondary amine, with hydrogen to form the bis(aminopropyl) aliphatic glycol.

There are significant advantages resulting from the improvement in the process, these are:

an ability to minimize byproduct formation caused by polymerization of acrylonitrile., an ability to eliminate many of the separation problems caused by the generation of byproducts having boiling points similar to the amine formed in the reaction; and an ability to minimize by-product formation caused by reaction of acrylonitrile with the hydrogenated cyanoethylated glycol:

DETAILED DESCRIPTION OF THE INVENTION

It is customary in the production of bis(cyanoethyl)aliphatic glycols to carry out the reaction under conditions that cyanoethylation is achieved at both of the hydroxyl group sites in the aliphatic glycol. Monocyanoethylation will result in the formation of a cyanoethoxy alkanol and when the cyano group is ultimately reduced, the resulting aminoalkanol is a chain terminator for polymer applications.

In accordance with this reaction, the aliphatic glycol is one generally having from about 2 to 20 carbon atoms and representative aliphatic glycols include ethylene glycol, propylene glycol, butylene glycol, etc ; and aliphatic ether glycols such as diethylene glycol, dipropylene glycol, dibutylene glycol and alkylene oxide derivatives of the aliphatic alcohols, e.g., of the ethylene glycol, propylene glycol, and butylene glycol. Such aliphatic glycols are widely used in the production of amines.

In the practice of this process, a stoichiometric excess of acrylonitrile is used vis-a-vis the aliphatic glycol to insure that cyanoethylation of each hydroxy group in the aliphatic glycol is achieved. As previously mentioned, it is imperative that substantially all of the hydroxy groups be converted to the cyanoethylated derivative because a hydroxy group in the final product results in the formation of a product which may act as a chain stopper in some end use applications. For purposes of this process at least 117% acrylonitrile of that stoichiometrically required for the conversion of all the hydroxy groups in the aliphatic glycol to the cyanoalkylated product is used, preferably at least 125%. As an upper limit, approximately 150% of the stoichiometric excess is suggested. Any level above this amount generally affords no significant advantages and requires removal of the acrylonitrile prior to hydrogenation.

In contrast to prior art processes, which generally involved neutralization of the cyanoethylated reaction product to prevent reversal of the reaction during the separation process, this process converts the residual acrylonitrile into a separable amine. Absent neutralization in the prior art, the cyanoethylated derivative sometimes cleaved at the ether oxygen reversing the reaction and generating the aliphatic glycol and olefinic nitrile. In the practice of this process an aliphatic primary or secondary amine having from 1 to 6 carbon atoms is added to the reaction product resulting from the reaction of acryolnitrile and aliphatic glycol. These primary and secondary amines react with the excess acrylonitrile to produce secondary and tertiary amine derivatives. Examples of aliphatic amines suited for reaction with acrylonitrile include methylamine, dimethylamine, ethylamine, diethylamine, propylamine, dipropylamine and so forth.

The reaction of residual acrylonitrile remaining after cyanoethylation of the aliphatic glycol with the amine can be carried out at a temperature of from about 0 to 50° C at a pressure of from 1 to 4 atm°. In a preferred practice the reaction is carried out at modest temperatures to prevent reversal of the cyanoethylated aliphatic glycol to its original reactant, i e., acrylonitrile and aliphatic glycol.

After substantially all of the acrylonitrile is reacted with the aliphatic amine, the hydrogenation of the cyanoethylated aliphatic glycol can be effected without separation of the reaction products. Hydrogenation is carried out in conventional manner, e.g., by contacting the cyanoethylated aliphatic glycol with hydrogen in the presence of a hydrogenation catalyst under hydrogenation conditions. Exemplary hydrogenation catalysts include Raney nickel, palladium. platinum, ruthenium, rhodium, and cobalt. Often ammonia is charged to the reaction zone to maintain high yield of the amino glycols and other derivatives The hydrogenation of the cyanoethylated derivative of the polyhydric alcohol may be carried out in the presence or absence of solvent. However, typically a solvent is used as it often enhances hydrogenation conditions. Examples of solvents include aliphatic alcohols such as methanol, ethanol, isopropanol or saturated hydrocarbons having from 5-12 carbon atoms such as hexane, cyclohexane, heptane, decane, etc. Temperatures of from 50 to 120° C at hydrogenation pressures of 500 to 2,000 psig are used to carry out the reaction. Further details are set forth in U.S. Pat. No. 4,313,004 and the subject matter of that patent is incorporated by reference, including the procedures for hydrogenation including the procedures described in the background portion of the patent.

After hydrogenation of the cyanoethylated aliphatic glycol, the reaction product may then be separated. In contrast to the prior art, the boiling point and aliphatic primary and secondary amine derivatives of acrylonitrile are substantially different from that of the bis-(aminopropyl) glycol resulting from the hydrogenation of the cyanoalkylated aliphatic glycol. Therefore, simple separation may be achieved through distillation.

The following examples are provided illustrate preferred embodiments and invention.

EXAMPLE 1

Preparation of bis(2-cyanoethoxy)ethane/dimethylaminoproplonitrile mixture

Into a 1 liter, 3-necked round-bottomed flask equipped with a thermometer, pressure-equalizing dropping funnel, reflux condenser and magnetic stir bar was placed 186 g (3.0 moles) of ethylene glycol and 1 g of anhydrous lithium hydroxide. The solution was warmed to 50° C and then with agitation 397.5 g (7.5 moles) of acrylonitrile were added dropwise over 90 min. while maintaining the temperature between 50 and 60° C Following addition Of the acrylonitrile. the reaction mixture was stirred an additional 90 min. at 50° C and then cooled and transferred to a 1 liter stirred autoclave. At this time it was concluded cyanoethylation was complete.

Conversion of residual acrylonitrile was converted to dimethylamino propionitrile (DMAPN) was achieved as follows. The contents of the autoclave were stirred at 25° C and 67.5 g (1.5 moles) of anhydrous dimethylamine was admitted to the autoclave over a 20 min. period while maintaining the reactor contents at 25° C by passing water through internal cooling coils. The reaction mixture was stirred for an additional 30 min. GC and NMR analysis of the crude product mixture revealed the composition to be 77.4 wt% of bis(cyanoethoxy)ethane, 21.9 wt% of DMAPN, 0.43 wt% of 2-cyanoethoxyethanol and 0.24 wt% of acrylonitrile.

EXAMPLE 2

Preparation of bis(3-aminopropoxy)ethane/dimethylaminopropylamine mixture

Into a 300 ml autoclave was placed 10 g of Raney cobalt and 15 g of anhydrous ammonia. A heel of 30 ml of -t-butanol was then pumped into the reactor and the reactor heated externally to 90 C. The pressure was then raised to B5O psig with hydrogen. The crude product mixture containing bis(2-cyanoethoxy)ethane and DMAPN from Example 1 was then pumped into the autoclave at a rate of 0.6 g/min until 150 g of the mixture had been admitted. During the addition, the temperature was maintained at 90° C. and the pressure at 850 psig. Following the addition. the reactor was stirred an additional 1 hr until hydrogen uptake was complete Analysis of the product mixture by GC (t-butanol free basis) revealed the composition to be 21.5 wt% DMAPA. 73.5 wt% of bis(3-aminopropoxy)ethane, 0.72 wt% of 3-aminopropoxyethanol, 1.2 wt% of N-(dimethylamino)-bis(3-aminopropoxy)ethane and 3.1 wt% of bis(aminopropoxyethoxypropyl)amine.

EXAMPLE 3

Distillation of bis(3-aminopropoxy)ethane and DMAPA

Distillation of the reaction product of Example 2 was performed in a 1" packed column with 12 theoretical plates. Distillation of 74B g of material was first begun at atmospheric pressure to remove 133 g of t-butanol. Then the distillation pressure was lowered to 200 torr to remove 127.1 g of DMAPA (78-82° C. @191 torr). Following the DMAPA cut, the pressure was slowly reduced to 24 torr to remove the transition cut of 104.1 g of a mixture of bis(3-aminopropoxy)ethane and 3-aminopropoxyethane and (120-151° C. @24 torr). This cut may be further reworked for recovery of the bis(3-aminopropoxy)ethane. The heart cut of 433.4 g of 99.9% pure bis(3-aminopropoxy)ethane (154° C. @23 torr) follows leaving a bottoms of 41.7 g of the total distillation charge.

The following summarizes the above examples:

EXAMPLE 1 shows that the dinitrile bis(cyanoethoxy)ethane is completely formed by the addition of excess acrylonitrile in a short time period. The excess acrylonitrile is removed from the medium by addition of dimethylamine in an amount stoichiometric to the excess acrylonitrile. Thus, the hazardous distillation and recycle of either unreacted acrylonitrile or 2-cyanoethoxyethanol is avoided.

EXAMPLE 2 shows that the bis(cyanoethoxy)ethane/DAPN mixture from Example 1 can be directly hydrogenated to bis(3-aminopropoxy)ethane and DMAPA with no antagonism of the species present with respect to rate or selectivity.

EXAMPLE 3 shows that pure DMAPA and pure bis(3-aminopropoxy)ethane may be obtained via distillation. That is, no impurities present in the coproduction mixture interfere with the separation of pure products from the mixture.

What is claimed is:

1. In a process for preparing a bis(aminopropyl) aliphatic glycol by reacting an aliphatic glycol with acrylonitrile to produce a bis(cyanoethyl) aliphatic glycol and then hydrogenating the resulting bis(cyanoethyl)aliphatic glycol to produce the corresponding bis(aminopropyl)aliphatic glycol, the improvement which comprises:

effecting a cyanoethylation reaction between acrylonitrile and said aliphatic glycol under conditions such that the acrylonitile is present in at least 117% of that stoichiometrically required for the bis(cyanoethylation), and reacting excess acrylonitrile from the cyanoethylation reaction of said aliphatic glycol with an aliphatic primary or secondary amine having from 1 to 20 carbon atoms, thereby essentially removing said acrylonitrile from said reaction medium: and then, hydrogenating the bis(cyanoethyl) aliphatic glycol to form said bis(aminopropyl) glycol.

2. The process of claim 1 wherein said aliphatic glycol has from 2-20 carbon atoms.

3. The process of claim 2 wherein said reaction of acrylonitrile and aliphatic glycol is conducted at a temperature from 30 to 70° C.

4. The process of claim 3 wherein said aliphatic amine used for reaction with said acrylonitrile in the reaction medium is a $C_1$-$C_6$ aliphatic primary or secondary amine.

5. The process of claim 1 wherein the acrylonitrile is present in an amount from 117 to 150% required for stoichiometric reaction with said glycol.

6. The process of claim 5 wherein said aliphatic glycol is ethylene glycol.

7. The process of claim 5 wherein said glycol is diethylene glycol.

8. The process of claim 5 wherein said amine is a methylamine.

* * * * *